United States Patent [19]
Cohen et al.

[11] Patent Number: 5,343,288
[45] Date of Patent: Aug. 30, 1994

[54] OPTICAL EVALUATION OF AUTOMOTIVE GLASS

[75] Inventors: Brian E. Cohen, Toledo; William M. Greenberg, Oregon; William V. Pagryzinski, Toledo; Brian E. Smith, Sylvania, all of Ohio

[73] Assignee: Libbey-Owens-Ford Co., Toledo, Ohio

[21] Appl. No.: 980,556

[22] Filed: Nov. 23, 1992

[51] Int. Cl.$^5$ ............................................. G01N 21/88
[52] U.S. Cl. ...................................... 356/239; 359/13
[58] Field of Search ............... 356/237, 239, 240, 430, 356/431, 243, 251–254; 250/562, 563, 571, 572; 358/106, 107, 103, 250; 362/217, 225, 250, 225, 285; 359/13, 15, 601, 630, 632; 340/705, 980; 434/42–44

[56] References Cited

U.S. PATENT DOCUMENTS

| | | | |
|---|---|---|---|
| 2,887,927 | 5/1959 | Newton | 356/252 |
| 4,082,463 | 4/1978 | Dehait et al. | 356/243 |
| 4,310,242 | 1/1982 | Genco et al. | 356/239 |
| 4,647,197 | 3/1987 | Kitaya et al. | 356/239 |
| 4,776,692 | 10/1988 | Kalawsky | 356/239 |
| 5,013,134 | 5/1991 | Smith | 359/360 |
| 5,157,549 | 10/1992 | Suzuki et al. | 359/360 |

*Primary Examiner*—Richard A. Rosenberger
*Assistant Examiner*—Hoa Q. Pham
*Attorney, Agent, or Firm*—Marshall & Melhorn

[57] ABSTRACT

A system for evaluating the head-up display aperture of a vehicle windshield with respect to established optical standards, independently of the projection system with which it is to be utilized. A fixture is provided for mounting a windshield in a predetermined position. An object plate having a series of accurately spaced parallel slits therethrough is positioned so that a light source positioned behind the object plate directs a series of narrow elongated light beams corresponding to the slits against the interior surface of the windshield within the display area. A line scan camera array system scans the display area and produces signals indicative of the apparent positions of the primary and secondary images of the beams reflected by the opposite surfaces of the windshield. The signals are transmitted to and stored within a computer system as a measured data base or map. An illuminated calibration plate identical to the object plate and positioned at the ideal virtual image plane of the windshield and camera system, is similarly scanned by the line scan camera array system in the absence of a windshield. The camera produces signals indicative of the positions of the lines and transmits them to the computer system for storage as a reference or calibration data base or map.

16 Claims, 2 Drawing Sheets

OPTICAL EVALUATION OF AUTOMOTIVE GLASS

BACKGROUND OF THE INVENTION

1. Field of the Invention

The present invention pertains generally to evaluation of optical characteristics of transparent glazing products, and more particularly to evaluation of automotive glass for compliance with established standards of optical quality. The invention has particular utility in the evaluation of windshields for incorporation in so-called automotive head-up display systems.

2. Description of the Prior Art

Head-up display systems are becoming increasingly popular as a safety and convenience feature on present day automotive vehicles. In such systems, vehicle operating information is projected onto a vehicle windshield and images are reflected into the operators forward field of vision. The operator can thus observe the field in front of the vehicle and the displayed operating information simultaneously. Head-up display systems have heretofore been utilized extensively in the aircraft industry, and to a lesser extent in the automotive field. Use of the system in the automobile minimizes the need for the operator to divert his or her attention from observation of the road ahead to make periodic observations of the dashboard display panel. The operator is therefore able to continuously focus attention on the road while simultaneously viewing essential vehicle operating information such as speed, fuel level, engine temperature, etc., thereby greatly enhancing the safety of vehicle occupants and others.

Despite the advantages of head-up display systems, in order for their use in automobiles to become widespread it will be necessary for the windshields employed in the systems to meet the stringent cost and quality requirements of the automotive industry. Present day automotive windshields comprise two sheets of curved glass integrally bonded to an interlayer of plastic, generally a sheet of polyvinyl butyryl. The geometry of the windshield unit is of critical importance in establishing the optical quality of the head-up display system. The windshield is, of course, installed in the vehicle in an inclined position so that the driver views the road ahead at a significant angle to the surfaces of the windshield.

The vehicle operating information is projected onto the windshield by a projector mounted beneath the dashboard of the vehicle, and is reflected from the inboard surface as a primary display image for viewing by the driver. A secondary display image of the projected information, of lesser intensity, is reflected from the outboard surface of the windshield. Because of the geometry of the windshield construction and the angle of installation in the vehicle, the secondary image may be displaced from the primary image as viewed by the driver so as to create a ghosting effect and make reading of the information difficult. In order to alleviate this problem, it has been proposed to fabricate the windshield so that the inboard and outboard surfaces, at least in the display area, are not parallel. In other words, the surfaces are disposed at a slight angle to one another, the angle being calculated in accordance with the angle of installation of the windshield to cause the primary and secondary reflected images as viewed by the driver to be substantially superimposed upon one another. This can be accomplished as disclosed, for example, in U.S. Pat. No. 5,013,134, by laminating the glass sheets to a sheet of interlayer material which is of a suitably tapered or wedged configuration.

Evaluation of head-up display windshields for compliance with established standards involves grading the unit in accordance with a number of performance criteria. Among the criteria are the relative head-up display image size and the amount of displacement between the images reflected from the inboard and outboard surfaces of the windshield. These criteria are functions of a number of parameters, including the vertical radius of curvature of the curved windshield in the display area, the wedge or non-parallelism between the inboard and outboard surfaces, and the windshield's slope, or angle of installation in the vehicle. Heretofore, evaluation has generally been accomplished by using an actual projector to simulate the environment in which the windshield is to be later employed in a vehicle, and then observing and evaluating the image produced. The head-up system, comprising both the projector and the windshield, is thus evaluated. When installed in a vehicle with a different projector, the display may differ considerably from that in the test system. A suitable system has not been available heretofore for quickly and accurately ascertaining the values of the pertinent parameters for the windshield per se, and evaluating the collected data to determine whether the head-up display area of the windshield complies with the established standards.

SUMMARY OF THE INVENTION

In accordance with the present invention, there is provided a system for quickly and accurately evaluating head-up display vehicle windows with respect to established optical standards, independent from the projection system with which it will be utilized. A mounting fixture is provided for receiving and accurately positioning a windshield to be evaluated. An object, preferably an opaque plate as of metal having a series of accurately spaced parallel elongated slits or openings cut therethrough, is positioned at a known distance from an orientation with respect to XYZ coordinates of the so-called gut ray intersection point for an ideal or computer modeled windshield. A calibration plate, which is a duplicate of the object plate of the object, is positioned at the ideal virtual image plane, which is a function of the vertical and horizontal radii of curvature object location and angle of installation of the windshield. The rear of the calibration plate is illuminated by high output light sources, and the lens of an adjustably mounted modular CCD (coupled charged device) line scan camera, is set to focus on the calibration plate. The camera is positioned so that the principal plane of the camera lens is at a predetermined referenced position or image distance from the calibration plate for the ideal windshield. The distances between the lines of the calibration plate are known, and therefore data indicative of the calibration angle per pixel in the line scan camera is collected and stored in the memory of an associated computer.

The calibration plate is removed and a windshield is placed in the mounting fixture. The object plate is illuminated by high output light sources to project a series of lines to the window unit. The windshield acts as a lens and creates a virtual image at some distance in front of the window unit. The line scan camera then observes the virtual image of the object plate, which appears as a series of primary and secondary images for each reflected line from the object plate at a particular lateral coordinate, and the observed information is transferred to the memory of the computer. The camera is indexed laterally a predetermined distance, and another image is observed and the information is transferred to the computer memory. The camera indexing and image recording are repeated until the entire display area has been examined and a data file for the display area has been created in the computer memory.

The stored data is reduced to its useable constituents by the computer, and the location of the center of intensity of the pixels for each primary and secondary reflected line is determined from the data. The precise vertical pixel location is thus known for each reflected primary line, and the vertical radius is determined by optical calculations based on the relative angle between adjacent reflected primary lines. Vertical pixel locations for the primary and secondary images of reflected lines are utilized for geometrically determining the wedge of the windshield at any particular location within the examined area, that is, the angle between tangents to the opposite front and rear surfaces of the unit. The attitude, or angle of installation of the window unit under test, may likewise be calculated from the stored data.

The quality of the windshield with respect to established head-up display standards is generally defined by two parameters, namely, magnification of the reflected image and displacement between the primary and secondary images. Magnification is a function of the vertical radius of the windshield, while displacement, which is defined as the amount of separation of the secondary image from the primary image, is a function of the radius and the wedge angle between the opposite surfaces. The computer is programmed to provide by means of a screen and/or a printer, area mapping of both parameters, and a comparison of the observed parameters with predetermined acceptable standards for the parameters.

BRIEF DESCRIPTION OF THE DRAWINGS

In the drawings, wherein like numerals refer to like parts throughout.

DESCRIPTION OF THE PREFERRED EMBODIMENT

Figure 1:
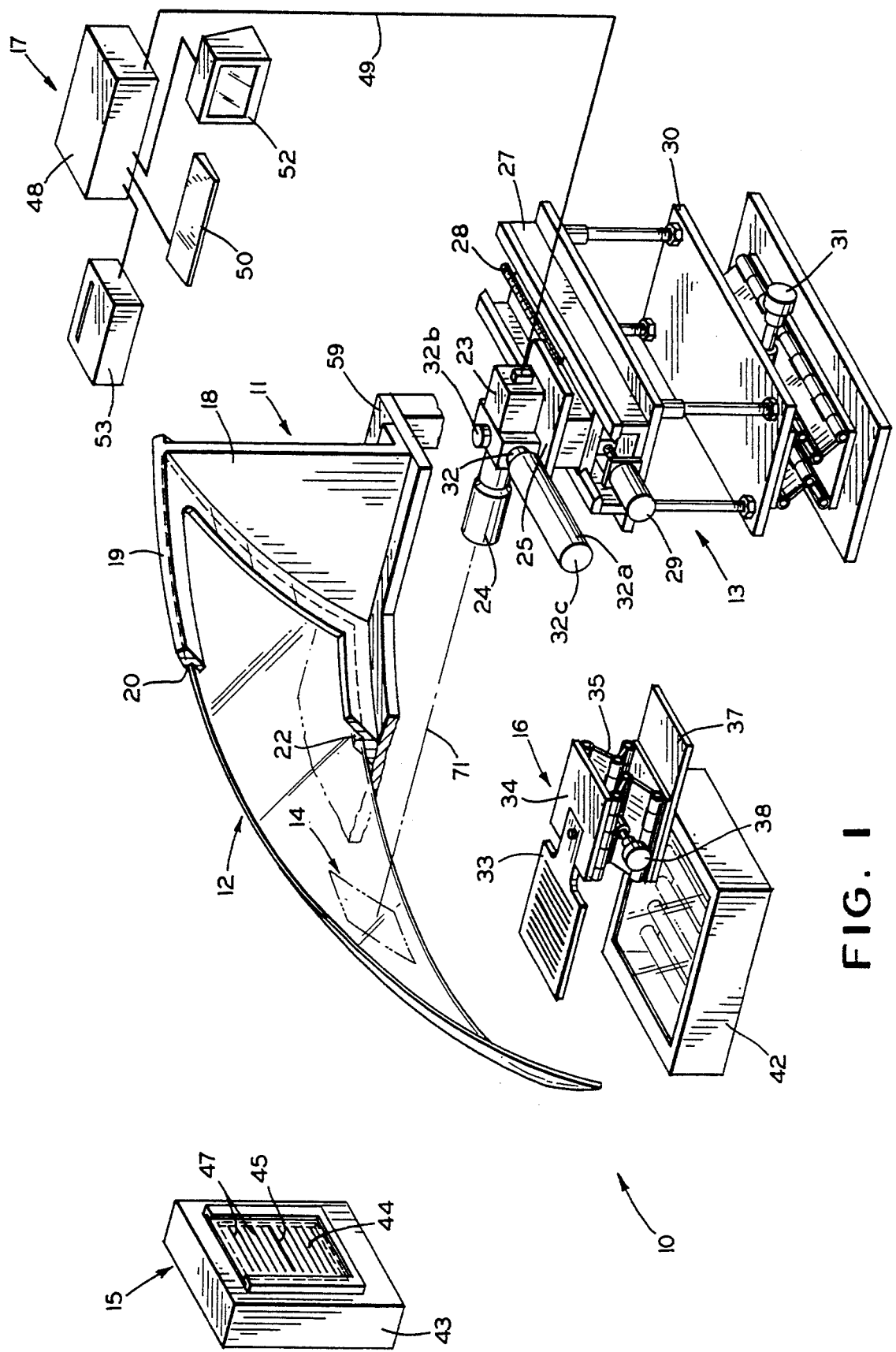
FIG. 1 is a schematic perspective view of a system embodying the invention for evaluating the head-up display area of an automotive windshield.

With reference to the drawings, and particularly to FIG. 1 thereof, there is illustrated generally in schematic form at 10 an inspection system in accordance with the invention. A mounting fixture or jig 11 supports a windshield 12 or other window unit in a predetermined fixed position within the inspection system. A modular ECD line-scan camera unit 13 is positioned behind the windshield so as to be able to observe a head-up display aperture 14 of the windshield. A calibration unit 15 is positioned in the field of the camera ahead of the windshield. A display unit 16 is positioned to project a suitable image pattern onto the aperture 14 for scanning by the camera. A computer system 17 is operatively coupled to the camera unit 13 for controlling operation of the camera unit and receiving, storing and processing data gathered by the camera. The mounting fixture 11, camera unit 13, calibration unit 15 and display unit 16 are preferably incorporated in a framework (not shown) as will be hereinafter described.

The mounting fixture or jig 11 includes a stand 18 having a generally rectangular opening defined by a support frame 19, a portion of which is shown in FIG. 1. A recessed portion 20 is provided in the support frame for receiving the peripheral margin of the windshield 12, whereby the windshield is supported in the attitude at which it would normally be installed in an automobile. The recess has an outline and configuration complementary to the peripheral margin of the windshield, and may include an upwardly projecting lip 22 extending along the lower edge, whereby a windshield to be inspected will assume the proper position for inspection when placed within the recess.

The head-up display system will, of course, be adapted for many different vehicle models presenting differing geometric configurations. In addition, each particular vehicle may be operated by drivers of varying heights so that the driver's perception of the display panel 14 will vary. In order to accommodate those variables and enable the inspection system to accommodate different windshields and observe the display from the perspective of different categories of drivers, the camera unit 13 is mounted for selected vertical positioning relative to the windshield, as well as traversing horizontal movement. Move particularly, as best seen in FIG. 1, a conventional modular line-scan camera 23 having a lens pack 24 is mounted upon a traversing base, identified generally at 25. The camera may, for example, be a model LC1902 Modular Line Scan unit made by EG&G Reticon of Sunnyvale, Calif. The base is carried upon a slide table 27 and is adapted to be incrementally moved to selected lateral positions by means of a screw 28 driven by a motor 29 controlled either manually or by the computer 17. The slide table 27, in turn, is suitably mounted upon an elevating stage 30 including an optical grade laboratory jack mechanism operable by an adjusting knob 31 for selectively raising and lowering the stage 30 and thus the camera 23. The camera preferably includes a port 32 for mounting an internal laser alignment unit and/or through-the-lens view finder 32a selectively activated by a mirror control knob 32b. A viewing port 32c may be provided for visually aligning the camera with the aperture 14 and the calibration unit 15 through the view finder.

The display unit 16 is positioned beneath the windshield 12 so as to project a series of precisely spaced horizontal lines toward the windshield. An object plate 33 is affixed to a platform 34 carried by a vertically adjustable elevating mechanism 35 upon a suitably supported base plate 37. The vertical position of the platform 34 and object plate 33 carried thereby may be adjusted by means of an adjusting knob 38 on the elevating mechanism 35.

Figure 2:
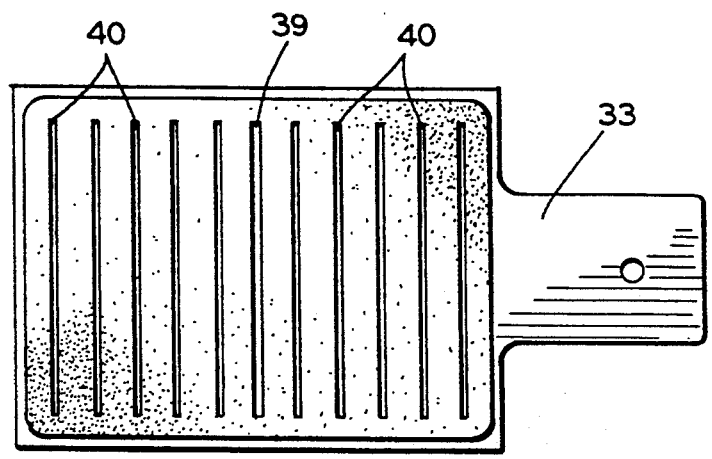
FIG. 2 is an enlarged plan view of the object plate illustrated in FIG. 1.

As best seen in FIG. 2, the object plate 33 is provided with a centrally located reference slit 39 and a series of spaced, parallel slits 40 on either side thereof, all extending through the plate. The slits 40 are of equal width, while the slit 39 is significantly broader than the slits 40 so as to produce a recognizable reference signal or position in the measured data. For example, the slits 39 and 40 may be spaced 0.50 inch (12 mm) apart on centers, with the slit 39 having a width of about 0.047 inch (1.2 mm) and the slits 40 having a width of about 0.030 inch (0.8 mm). A light box 42, preferably a very high output source with a regulated power supply to equalize the intensity profile, is positioned beneath the object plate 33 for directing light upwardly through the slits to project corresponding beams onto the windshield 12 within the aperture area. The images of the beam from the slit 39 reflected from the opposite surfaces of the windshield 12 will, of course, be correspondingly wider than those from the slits 40 so as to serve as a reference point in analyzing the observed and recorded data. The light box may be suitably mounted as on rails (not shown) for movement in a direction transverse to the slots for movement into and out of operative position and for alignment beneath the slots. The light box may also conventionally be supplied with cooling fans (not shown).

The calibration unit 15 is employed in calibrating the inspection system initially, and subsequently at such times as recalibration may be necessary. To that end, the calibration unit may comprise a portable light box 43 including a high intensity light source therewithin (not shown) and a calibration plate 44 adapted to face the windshield 12 and the camera unit 13. The calibration plate is, in effect, a duplicate of the object plate in that it includes a reference slit 45 and additional parallel slits 47 equal in number, width and spacing to the slits 39 and 40, respectively.

For purposes of calibrating the camera 23, the light box 43 is positioned opposite the mounting fixture 11 from the camera, with no windshield on the mounting fixture. More particularly, the light box may preferably be positioned at a predetermined reference location upon a structure to be hereinafter described upon which the other components are mounted, as by means of conventional locating pins. The light box is positioned so that the calibration plate is located at the ideal virtual image plane of the object plate, which is a function of the theoretical vertical and horizontal radii of curvature of a windshield to be inspected. The lens of the CCD line scan camera is set to focus on the calibration plate, and the camera is moved along the optical axis of the lens so that the primary principal plane of the lens pack is at a predetermined image distance from the calibration plate. The distance between the lines or slits of the calibration plate is known, and therefore a calibration angle per pixel in the line scan camera can be determined and stored in the computer memory. Thereafter the calibration unit 15 can be deactivated and removed from the area to prepare the system for inspection of windshields.

The computer system 17 is operably connected to the camera unit 13 for both controlling operation of the camera 23 and receiving, storing and analyzing data observed by the camera. To that end, the computer system includes a central processing unit 48 suitably coupled to the camera unit by a line 49. The computer system further includes a keyboard 50 for accessing the processing unit 48, a screen 52 for visually displaying observed data, and a printer 53 for printing out test results, all suitably operably connected to the processing unit.

Figure 3:
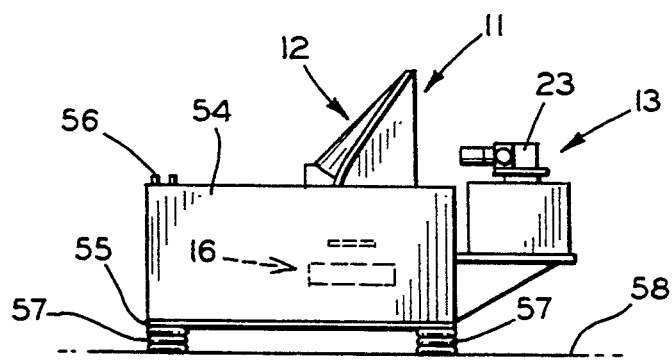
FIG. 3 is a schematic side elevation of apparatus in accordance with the invention.

The optical section of the inspection system is, of course, sensitive to vibration. Thus, it is desirable that the windshield 12, the camera unit 13, the calibration unit 15, and the display unit 16 be isolated from extraneous vibrations which may occur due to activities in the area around the inspection system. In order to minimize the effect of such vibrations, as will be seen in FIG. 3 the aforementioned components are preferably carried by a suitable structure 54 upon an air table 55 supported at its corners by adjustable air bladders 57 resting upon a floor 58 or other supporting surface. Locating pins 56 may be provided on the structure 54 for reception in cooperating recesses (not shown) in the base of the calibration unit for properly locating the calibration unit upon the structure. The air bladders conventionally include means (not shown) by which they can be selectively inflated or deflated to level the air table. The air table thus serves to both level the inspection system and to absorb and damp any vibrations present in the adjacent structure.

Figure 4:
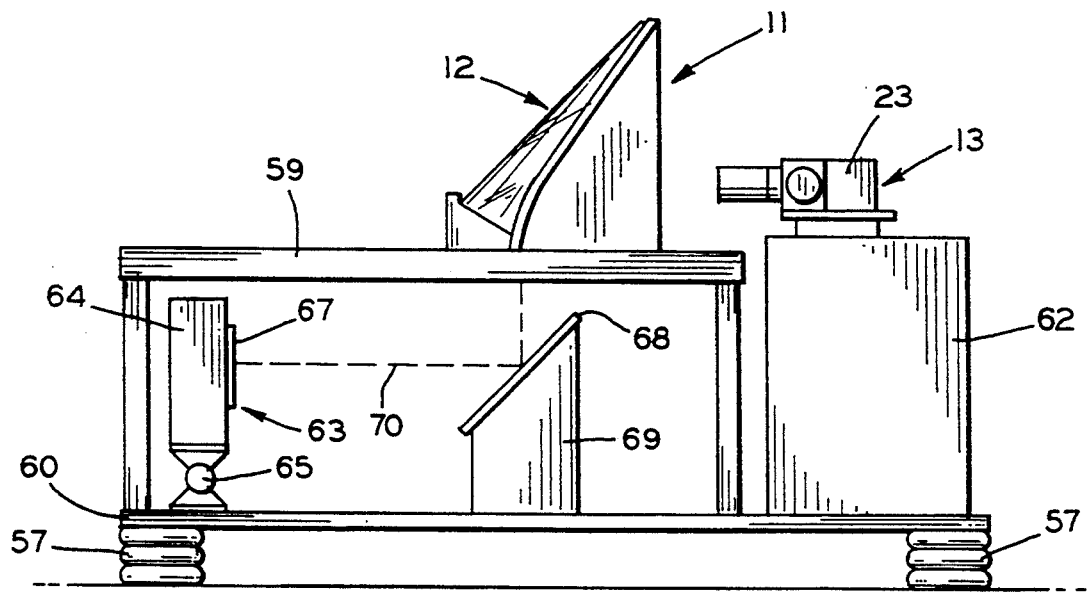
FIG. 4 is an enlarged schematic side elevation, similar to FIG. 3, illustrating an alternate embodiment of the apparatus.

There is shown in FIG. 4 an alternate embodiment wherein the object plate and the light box are mounted in a vertical position and displaced from beneath the mounting fixture carrying the windshield to be inspected. In the alternate embodiment the mounting fixture 11 is supported upon a suitable framework 59 carried upon an air table 60 again supported at its corners by adjustable air bladders 57 resting upon the floor 58. The camera unit 13 is carried upon a base unit 62 at the rear of the air table. A display unit, shown generally at 63 and equivalent to the display unit 16 of the preferred embodiment, is positioned at the forward end of the air table and includes an upstanding light box 64 carried, as by a suitable conventional six axis laboratory stage 65, upon the air table. An object plate 67 equivalent to the plate 33 is positioned so as to be illuminated by the high intensity light sources within the light box. Light beams are directed through the slits (not shown) of the object plate to a mirror 68 supported at a suitable reflective angle by a mirror stand 69 on the air table 60. Thus, as shown in broken line in FIG. 4, light beams 70 from the object plate are reflected by the mirror 68 to strike the display aperture of the windshield 14 and create images for observation by the camera 23.

Summarizing operation of the invention, the table upon which the components of the inspection system are carried is initially levelled by manipulation of the adjustable air bladders 57. Thereafter, the camera 23 is aligned within the system. A reference windshield having the head-up display aperture accurately determined and outlined thereon is placed in the mounting fixture 11. The viewing port 32c is utilized to approximately align the components. The camera laser light source is activated and a laser beam indicated in broken line at 71 in FIG. 1, is directed through the lens 24 of the camera toward the display aperture. The camera is positioned vertically by means of the stage 30 so that the laser beam, and hence the optical axis of the camera, is aligned with the position at which the image from the reference slit 39 will appear during subsequent examination of windshields.

The laser is then turned off and the through-the-lens view finder within the camera is returned to its normal inoperative position. The reference windshield is removed from the mounting fixture, and the calibration unit 15 is appropriately positioned and the lights in the box 43 are turned on to illuminate the slits 45 and 47 in the calibration plate 44. The camera 23 is focused on the calibration plate, and the plate is moved along the optical axis as necessary to position the focal plane of the lens pack 24 at a predetermined distance from the calibration plate. The camera 23 then scans or takes a picture of a vertical segment of the calibration plate by means of the pixel array within the camera, with the individual pixels of the array outputting an appropriate signal in response to light from each of the slits 45 and 47. This information is transferred to and stored in the central processing unit 48 of the computer system 17 for reference purposes. The camera is then indexed laterally a predetermined increment by the screw 28 and the motor 29 of the slide table 27 in response to a signal from the computer, and the scanning by the camera is repeated. The indexing is repeated so that the camera scans vertical segments entirely across the calibration plate and a composite picture or data file of the calibration plate is stored in the central processing unit 48. By way of example, the camera preferably begins scanning adjacent one edge of the calibration plate and is indexed in 0.6 inch (15 mm) increments across the plate. The display aperture, and thus the calibration and object plates, are on the order of six inches in width and nine inches in height (150 mm by 225 mm) so that the camera may advance in ten increments of 0.6 inch (15 mm) and then return to the starting point.

Following calibration, the calibration unit 15 is deactivated and a windshield 12 to be inspected is placed on the mounting fixture. The light box 42 of the display unit 16 is illuminated to project beams of light through the slits 39 and 40 of the object plate to the display panel 14 of the windshield. The camera 23 is operated through a cycle as heretofore described for calibration purposes, whereby the pixel array within the camera creates signals indicative of the apparent positions of the virtual images created by the light from each slit 39 and 40 reflected by the opposite surfaces of the windshield. The signals are transmitted to the central processing unit 48 for storage and processing, and creation of a data file or composite electronic picture of the positions of the primary and secondary images observed by the camera.

By appropriately processing this data with that of the calibration procedure, a numerical enumeration of the pertinent parameters of magnification and displacement is created in the form of a map of the inspected area. This map is compared by computer modelling with a corresponding map indicative of acceptability criteria parameters to determine whether the inspected unit falls within predetermined standards for acceptability. Processing of the data may occur simultaneously with the inspection, or the stored data may be processed subsequently to permit inspection of another windshield to proceed.

Inspection of the aperture from a single perspective has been described, that is, from the perspective of a single line of sight from the camera. However, it is fully contemplated that the area may be inspected from different perspectives to more nearly approximate the conditions actually presented by vehicle drivers. For example, a driver of a particular height may view the head-up display while looking straight ahead, or essentially horizontally. The display may also be observed while the driver is looking above or below the straight ahead position. Likewise, the height of individual drivers of a particular vehicle model will vary by a considerable amount, so that each will view the display from a different perspective. Accordingly, the display area may be inspected from a number of different perspectives by appropriately positioning the camera 23. For example, it is contemplated that standards may be established whereby the display area is inspected from the perspective of categories of drivers classified as short, medium and tall, each viewing the head-up display while looking up, looking straight ahead and looking down, or a total of nine perspectives. alternatively, the evaluation from the different perspectives can be accomplished by computer modelling upon the basis of observations from a single perspective.

While the invention has been described with respect to evaluation of head-up display panels of automotive windshields, it will be appreciated that it will find utility as well in evaluation of the optical quality of transparent sheet material in general, and other automotive glass in particular.

It is to be understood that the forms of the invention herewith shown and described are to be taken as illustrative embodiments only of the same, and that various changes in the shape, size and arrangement of parts, as well as various procedural changes, may be resorted to without departing from the spirit of the invention.

What is claimed is:

1. A method of evaluating a transparent sheet having spaced first and second major surfaces for optical quality comprising: supporting the sheet in a fixed position, directing a first plurality of narrow elongated beams of light spaced at known distances from one another at an angle against the first major surface of said sheet, whereby primary and secondary images of said beams are formed at a virtual image plane by reflection from said first and second surfaces, respectively, scanning said first and second images with a line scan array to generate signals indicative of the apparent positions of said first and second images of said elongated beams, storing the signals indicative of said apparent positions, directly scanning a pattern of said elongated beams of light at the virtual image plane similar to said first plurality of beams in the absence of said transparent sheet to generate signals indicative of the positions of said beams of incident light at the virtual image plane of an ideal transparent sheet, and comparing the signals indicative of the observed positions of the reflected primary and secondary light beams to the signals indicative of the ideal positions of the light beams to evaluate the optical quality of said transparent sheet.

2. A method for evaluating the optical quality of a transparent sheet as claimed in claim 1, including observing the reflected primary and secondary images of the beams of light within a first segment extending transversely across the plurality of spaced elongated beams, and thereafter observing the reflected primary and secondary images within a second segment extending transversely across the plurality of spaced elongated beams and displaced laterally from said first segment.

3. A method for evaluating the optical quality of a transparent sheet as claimed in claim 2, including observing the reflected primary and secondary images in a plurality of said bands entirely covering a predetermined area of said transparent sheet.

4. A method for evaluating the optical quality of a transparent sheet as claimed in claim 3, wherein said transparent sheet is an automobile windshield.

5. A method for evaluating the optical quality of a transparent sheet as claimed in claim 4, wherein said predetermined area is a head-up display aperture in said windshield.

6. Apparatus for evaluating the optical quality of a transparent sheet having spaced first and second major surfaces, including support means for supporting a said sheet in a predetermined position, a display unit for directing a first array of spaced, narrow elongated beams of light against said first surface at an angle thereto to form spaced virtual primary and secondary images of each beam of light by reflection from the first and second surfaces, respectively, at a virtual image plane, a line scan array means positioned to observe the reflected primary and secondary images and generate signals indicative of the apparent transverse positions of said first and second images, means for storing said signals, a calibration unit adapted to be positioned at the virtual image plane of a hypothetical sheet presenting desired optical characteristics and exhibit a second array of spaced narrow elongated beams of light similar to the first beam array of said display unit, said line scan array means being positioned to observe the second beam array of the calibrating unit directly in the absence of said glass sheet and generate signals indicative of the actual position of the beams in said second array for transmittal to said means for storing signals as reference signals.

7. Apparatus for evaluating the optical quality of a transparent sheet as claimed in claim 6, wherein said display unit comprises an object plate having a plurality of spaced parallel slits extending therethrough, and light means positioned behind said object plate for illuminating said object plate and directing said beams of light from said slits toward said first surface.

8. Apparatus for evaluating the optical quality of a transparent sheet as claimed in claim 7, wherein an intermediate one of said spaced parallel slits is of a first width, and the remainder of said slits are of a second width different from said first width, whereby the beam of light emanating from said intermediate slit produces an identifying signal distinguishable from the signal produced by the other of said slits.

9. Apparatus for evaluating the optical quality of a transparent sheet as claimed in claim 6, including a support structure upon which said sheet support means, said display unit and said line-scan array means are mounted, said sheet support means, display unit and line-scan array means being positioned on said support structure so as to be in operative relationship relative to one another.

10. Apparatus for evaluating the optical quality of a transparent sheet as claimed in claim 9, wherein said support structure includes a base supported upon adjustable bladders for levelling said base and isolating said base and support structure from external vibrations.

11. Apparatus for evaluating the optical quality of a transparent sheet as claimed in claim 9, wherein said sheet support means comprises a frame defining an opening generally conforming in outline and curvature to the peripheral marginal portion of said sheet, said frame including a recessed portion for receiving said peripheral marginal portion to support said sheet in said operative relationship.

12. Apparatus for evaluating the optical quality of a transparent sheet as claimed in claim 9, including a vertically adjustable elevating mechanism upon said structure, said display unit comprising an object plate having a plurality of parallel slits extending therethrough, and light means positioned behind the object plate, said object plate being carried upon said vertically adjustable elevating mechanism.

13. Apparatus for evaluating the optical quality of a transparent sheet as claimed in claim 9, including a slide table carried by said support structure, and means mounting said line-scan array means on said slide table for movement to selected lateral positions.

14. Apparatus for evaluating the optical quality of a transparent sheet as claimed in claim 13, including a screw member operably interconnecting said slide table and said means mounting said line-scan array, and means for rotating said screw member to selectively advance and retract said line-scan array mounting means across said slide table.

15. Apparatus for evaluating the optical quality of a transparent sheet as claimed in claim 14, including an elevating stage, said slide table being carried upon said elevating stage, and jack means operable to raise and lower said stage.

16. Apparatus for evaluating the optical quality of a transparent sheet as claimed in claim 9, including locating means on said support structure for cooperating with corresponding locating means on said calibration unit for positioning said calibration unit at a predetermined position on said support structure.

* * * * *